United States Patent [19]

Russell et al.

[11] Patent Number: 5,800,384
[45] Date of Patent: Sep. 1, 1998

[54] MULTI-LUMEN PERCUTANEOUS INTRODUCER

[75] Inventors: Michael A. Russell, Woburn; Arthur S. Lynch, Westwood, both of Mass.

[73] Assignee: Medical Parameters, Inc., Woburn, Mass.

[21] Appl. No.: 828,231

[22] Filed: Apr. 3, 1997

Related U.S. Application Data

[63] Continuation of Ser. No. 134,189, Oct. 8, 1993, abandoned.

[51] Int. Cl.$^6$ ............................................. A61M 3/00
[52] U.S. Cl. ............................................. 604/43; 604/164
[58] Field of Search .......................... 604/43, 164, 167, 604/264, 283, 284, 280, 51–53

[56] References Cited

U.S. PATENT DOCUMENTS

| | | | |
|---|---|---|---|
| 4,417,886 | 11/1983 | Frankhouser et al. | 604/53 |
| 4,493,707 | 1/1985 | Ishihara | 604/164 |
| 4,808,156 | 2/1989 | Dean | 604/43 |
| 4,857,062 | 8/1989 | Russell | 604/256 |
| 4,968,307 | 11/1990 | Dake et al. | 604/264 |
| 5,011,478 | 4/1991 | Cope | 604/165 |
| 5,025,778 | 6/1991 | Silverstein et al. | 128/4 |
| 5,066,285 | 11/1991 | Hillstead | 604/164 |
| 5,067,497 | 11/1991 | Greear et al. | 128/207.15 |
| 5,078,701 | 1/1992 | Grassi et al. | 604/264 |
| 5,104,389 | 4/1992 | Deem et al. | 604/264 |
| 5,106,368 | 4/1992 | Uldall et al. | 604/43 |
| 5,149,330 | 9/1992 | Brightbill | 604/280 |
| 5,167,623 | 12/1992 | Cianci et al. | 604/43 |
| 5,195,962 | 3/1993 | Martin et al. | 604/43 |
| 5,209,741 | 5/1993 | Spaeth | 604/264 |
| 5,215,527 | 6/1993 | Beck et al. | 604/164 |
| 5,219,335 | 6/1993 | Willard et al. | 604/164 |
| 5,221,256 | 6/1993 | Mahurkar | 604/43 |
| 5,236,424 | 8/1993 | Imran | 604/280 |
| 5,242,410 | 9/1993 | Melker | 604/164 |
| 5,250,038 | 10/1993 | Melker et al. | 604/264 |
| 5,328,480 | 7/1994 | Melker et al. | 604/164 |
| 5,342,295 | 8/1994 | Imran | 604/43 |

*Primary Examiner*—Robert A. Hafer
*Assistant Examiner*—Benjamin K. Koo
*Attorney, Agent, or Firm*—Hamilton, Brook, Smith & Reynolds, PC

[57] ABSTRACT

A multi-lumen percutaneous introducer for introducing a catheter and fluids into a body lumen includes an introducer sheath having a first lumen for receiving a catheter and a second lumen within the sheath having a proximal opening for receiving fluids and a distal opening for delivering fluids into the body lumen. A port in alignment with the first lumen receives the catheter when the catheter is inserted through the first lumen into the body lumen.

11 Claims, 3 Drawing Sheets

MULTI-LUMEN PERCUTANEOUS INTRODUCER

This application is a continuation of co-pending application Ser. No. 08/134,189 filed on Oct. 8, 1993, which is incorporated herein by reference in its entirety.

BACKGROUND

Catheters are commonly introduced into body lumens by first inserting a hollow needle through the skin into the desired body lumen. A guidewire is then inserted through the needle and advanced up the body lumen toward a desired location. The needle is then removed leaving the guidewire in the body lumen. A dilator is then inserted through the sheath of a catheter introducer. The catheter introducer and the dilator are then directed by the guidewire into the body lumen until the sheath of the catheter introducer reach a desired position. The guidewire and the dilator are removed leaving the sheath of the catheter introducer in the body lumen. A catheter is then inserted through the catheter introducer and advanced through the sheath into the body lumen.

Currently, in some medical applications, catheters have multiple lumens such that fluids can be delivered to a site in a body lumen. In some applications requiring catheter insertion and delivery of fluids, medical specialists use two introducers side-by-side. One introducer is employed for inserting a Swan-Ganz catheter, for example, while the second introducer is employed for inserting a fluid volume line. This technique is expensive as well as time-consuming because the physician must use two introducers.

Accordingly, there is a continuing need for an apparatus and method of positioning a catheter and to deliver fluids in an easier and less costly manner.

SUMMARY OF THE INVENTION

The present invention provides a multi-lumen percutaneous introducer for introducing a catheter and fluids into a body lumen. The introducer includes an introducer sheath having a first lumen extending within the sheath for receiving a catheter. The first lumen has a proximal opening and a distal opening through which the catheter can be passed. A second lumen within the sheath has a proximal opening for receiving fluids and a distal opening for delivering fluids into the body lumen. An introducer port in alignment with the first lumen receives the catheter when the catheter is inserted through the first lumen.

In preferred embodiments, the sheath is made of extruded polyurethane or equivalent materials. This material is sufficiently stiff to maintain patency of each lumen, yet flexible enough to permit bending of the sheath during insertion through a patient's skin and during catheter insertion. A valve assembly is in alignment with the first lumen and the introducer port. The valve assembly is in fluid communication with and is capable of sealing the first lumen. A side port delivers fluid into the first lumen. A directional valve coupled in fluid communication with the side port directs fluid into the side port from various fluid sources.

In another preferred embodiment, three or more lumens of the same or varying diameters can be included within the sheath with exit ports positioned on the same or different sides of the sheath. Additionally, each fluid delivery lumen can have multiple exit ports.

The present invention provides a simple and less costly apparatus and method for introducing a catheter and fluids into a body lumen. The present invention introducer positions both a catheter and a fluid line within a body lumen all within one introducer, thereby saving about half the time and cost of previous methods.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

Figure 1:
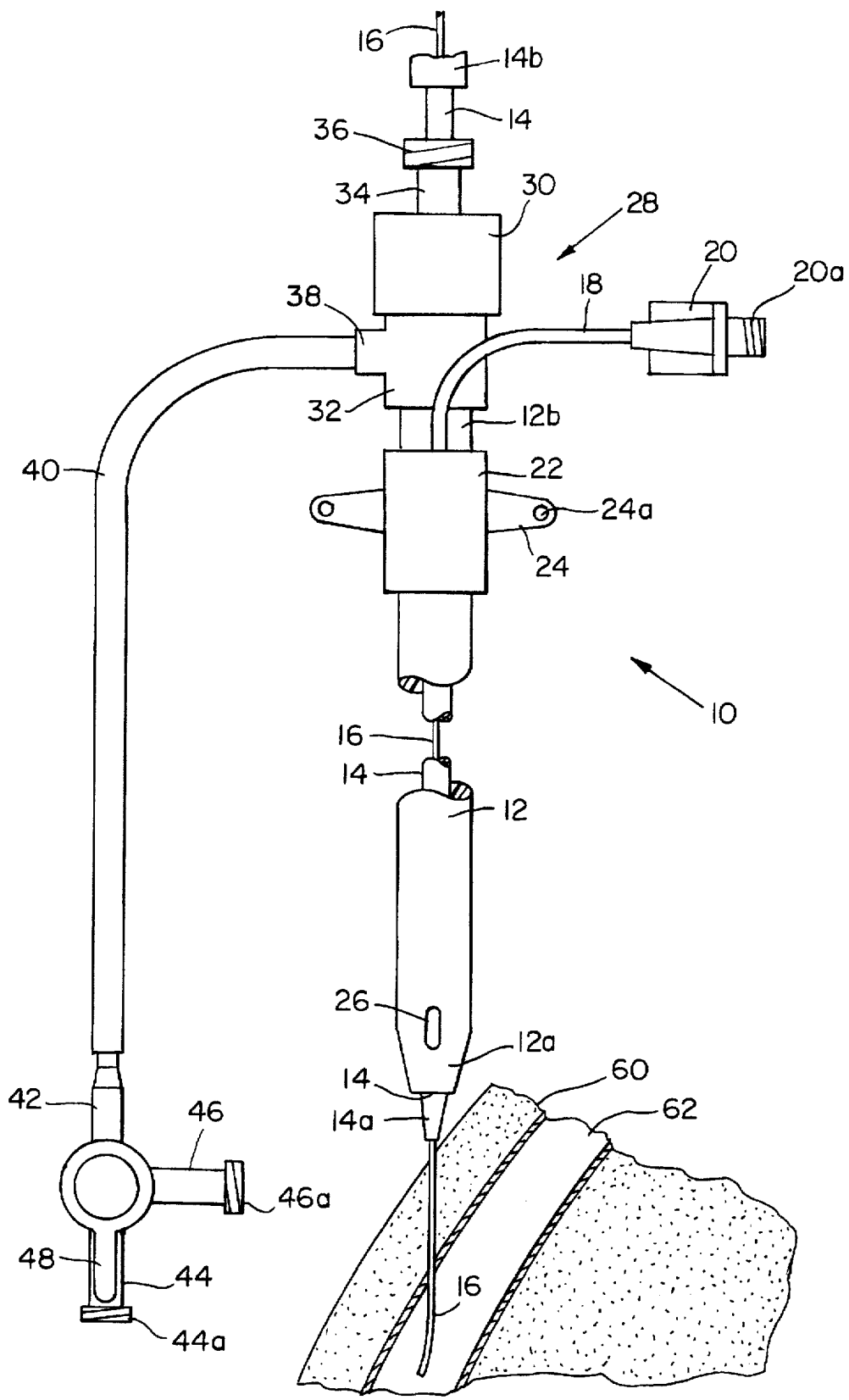
FIG. 1 is a front view of the present invention multi-lumen percutaneous introducer with the guide wire inserted into a body lumen.
Figure 2:
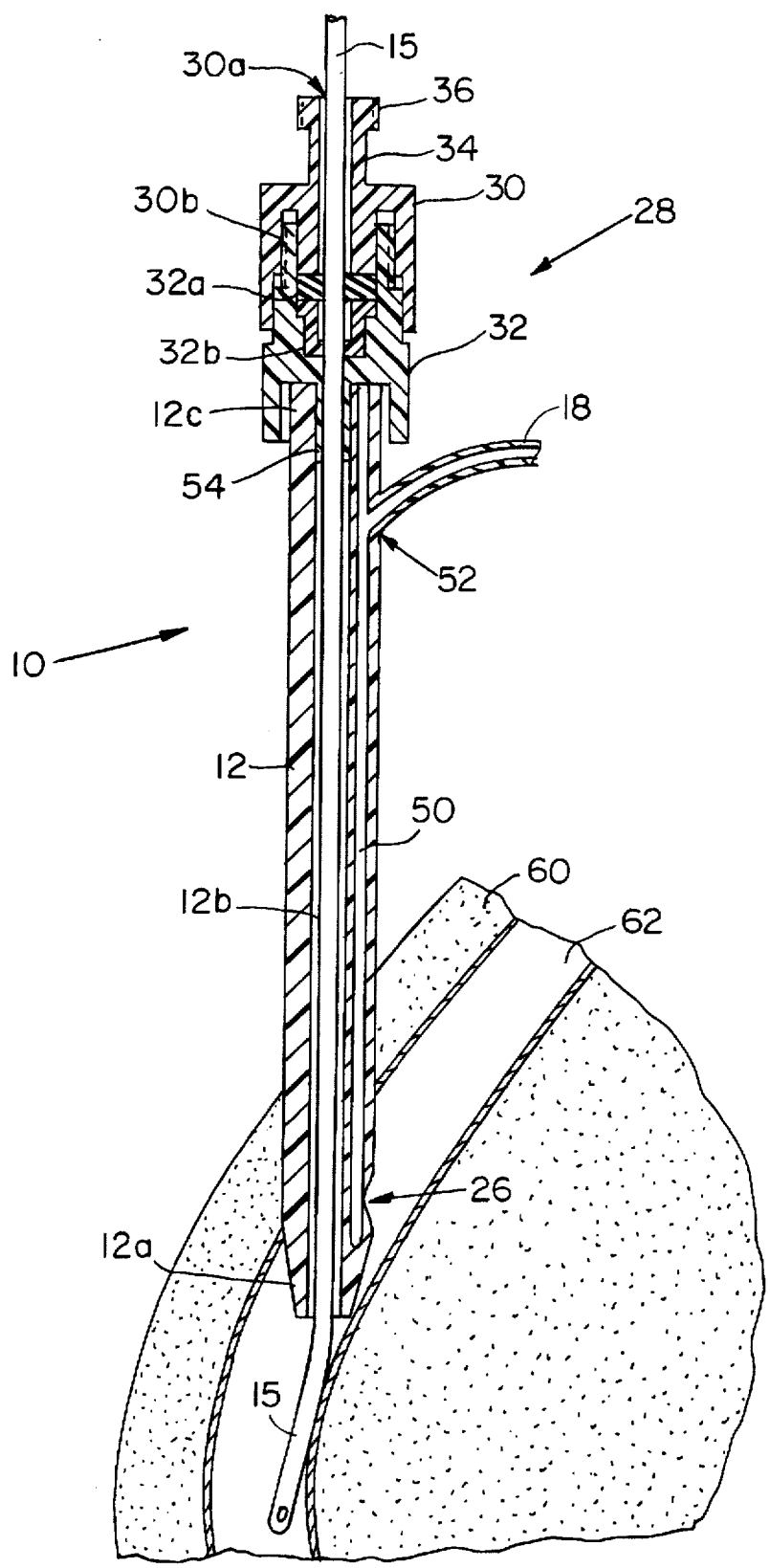
FIG. 2 is a sectional view of the present invention introducer showing a catheter being inserted into the body lumen and showing the side lumen.
Figure 3:
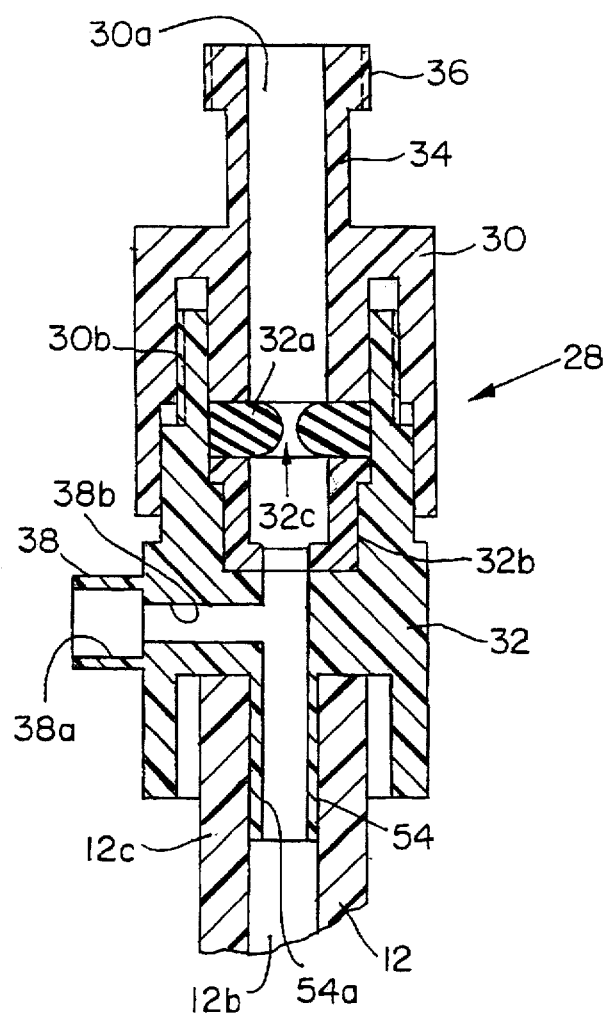
FIG. 3 is an enlarged sectional view of the valve assembly showing the side port.

In FIGS. 1, 2, and 3 introducer 10 includes a flexible plastic sheath 12 which has a central lumen 12b through which a dilator 14 and guidewire 16 or a catheter 15 can be inserted. Sheath 12 is coupled to a valve assembly 28 which is capable of sealing lumen 12b from passage port 30a when dilator 14 or catheter 15 passes through valve assembly 28 and sheath 12. A side lumen 50 for delivery fluids is located within the wall of sheath 12. Tubing 18 is coupled to sheath 12 and is in fluid communication with side lumen 50 via opening 52. Lumen 50 has an opening 26 located near tip 12a of sheath 12 allowing fluids within lumen 50 to exit. A side port 38 on valve assembly 28 allows fluids to be delivered to central lumen 12b via tubing 40 and multi-ported valve 42.

In operation a needle (not shown) is first inserted through tissue 60 into a desired body lumen 62. Guide wire 16 is then inserted through the needle into body lumen 62 and the needle is removed. Dilator 14 is then inserted through port 30a of valve assembly 28 and lumen 12b of sheath 12 (FIG. 1). Dilator 14 and introducer 10 are then directed by the guidewire 16 into a desired position within body lumen 62. Both the guidewire and the dilator are removed, leaving only sheath 12 of introducer 10 present in body lumen 62. A catheter 15 (FIG. 2) can then be advanced through the introducer 10 into body lumen 62. Fluids can then be introduced into body lumen 62 through lumen 12b via side port 38 (FIG. 3) or port 30a. Additionally, fluids can also be introduced into body lumen 62 via tubing 18 and side lumen 50.

A more detailed description of introducer 10 is given below. Sheath 12 is flexible plastic which is preferably made of extruded polyurethane or other equivalent extruded materials. Alternatively, sheath 12 can be made of expanded fibrous plastic such as fibrous expanded polytetrafluoroethylene (PTFE) or fibrous expanded polyurethane. Tip 12a may be molded as a unitary part of sheath 12 by placing a tip mold around the distal end of an extruded tube which serves as the body of sheath 12. Plugs of thermoplastic material may then be inserted into a distal end of one of the lumens before forming the tip by thermoforming or radio frequency energy. An opening 26 to side lumen 50 near tip 12a is then formed by remaining material on the surface of sheath 12 to expose a region of side lumen 50.

Tubing 18 delivers fluids to side lumen 50. Tubing 18 is inserted into a hole 52 and bonded to sheath 12 with a solvent. A mandrel (not shown) is inserted into lumen 12b and expanded to locate lumen 50 and tubing 18 in proper position with respect to each other. Additionally, a mandrel can also be inserted into side lumen 50. An optional band 22 can be bonded around sheath 12 and tubing 18 to hold tubing 18 firmly in place tubing 18 will not easily separate from sheath 12. Band 22 has flanges 24 with holes 24a which can be used to secure introducer 10 to other equipment. A connector 20 coupled to tubing 18 has a threaded portion 20a for coupling tubing 18 to a fluid source.

Valve assembly 28 is similar to that described in U.S. Pat. No. 4,857,062 which is herein incorporated by reference. Sheath 12 is coupled to valve assembly 28. End 12c of sheath 12 is coupled to valve assembly 28 by inserting connector 54 into central lumen 12b. Connector 54 has a slightly larger outer diameter than the diameter of lumen 12b so that when sheath 12 is stretched over connector 54, a secure fit is provided. Valve assembly 28 includes a lower portion 32 and an upper portion 30 which are coupled together by threads 30b. By rotating upper portion 30 relative to lower portion 32 so that portions 30 and 32 are brought closer together, valve member 32a is compressed and flattened against valve member 32b which closes off passage way 32c. This seals port 30a from central lumen 12b and also can seal catheter 15 or dilator 14 when passed through introducer 10. Connector 34 extends from upper portion 30 and has a threaded portion 36 for coupling valve assembly 28 to a fluid supply.

Side port 38 is in fluid communication with central lumen 12b via passage ways 38b and 54a. Tubing 40 is coupled to side port 38 by bonding tubing 40 within bore 38a with solvent. Multi-port valve 42 provides side port 38 with fluids via tubing 40. Multi port valve 42 has two connectors 44 and 46 respectively. Threaded portion 44a couples connector 44 to one fluid source while threaded portion 46a couples connector 46 to another fluid source. Valve lever 48 can be rotated to allow fluid to pass through one or both connectors 44 and 46 into tubing 40.

Fluids introduced through side lumen 50, side port 38 and port 30a can be drugs or biocompatible solutions. Since side lumen 50 is separate from central lumen 12b, drugs or solutions which are incompatible with those delivered through central lumen 12b can be delivered through side lumen 50 into body lumen 62. One application involves the insertion of a Swan-Ganz catheter into a patient's arterial system. Such catheters have a balloon on the distal end which can be inserted through the heart to a pulmonary artery and used to monitor blood pressure at the desired location. It is often desirable to deliver drugs into the artery during emergency procedures without having to make a second entry into the arterial system at a different site and without withdrawing the catheter previously inserted through the introducer. For a standard Swan-Ganz catheter having a 7.5 F outer diameter, it is preferable to have a first lumen with an inner diameter of 8.5 F or larger. This permits delivery of a second fluid through tubing 40. The tubing 40 and/or the tubing 18 are preferably at least 14 gauge minimum to deliver a large volume of medication as required.

The sheath 12 is generally less than 30 centimeters long, and preferably less than 20 centimeters. The sheath and valve assembly are made of biocompatible materials and form a disposable unit. The sheath and valve assembly form a kit with the dilator and guidewire.

Figure 4:
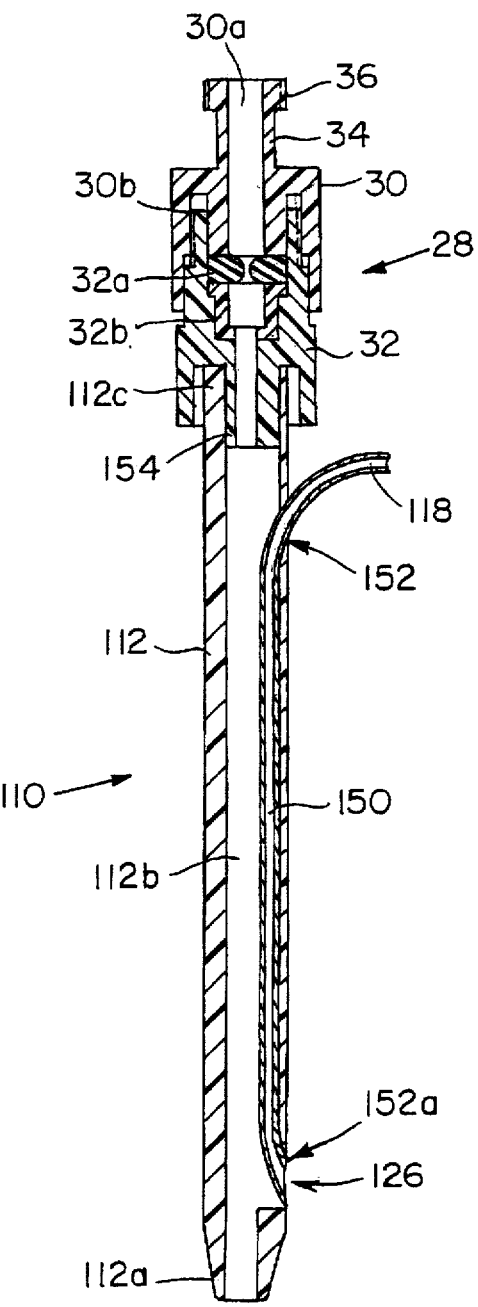
FIG. 4 is a side sectional view of another preferred embodiment of the present invention multi-lumen percutaneous introducer.

FIG. 4 depicts introducer 110 which is another preferred embodiment of the present invention. Sheath 112 is an extrusion having a single lumen 112b. Side lumen 150 is formed by inserting a length of tubing 118 through a hole 152 and passing the tube 118 through lumen 112b. End 112c is coupled to connector 154 of valve assembly 28. Tubing 118 is brought through hole 152a near tip 112a. Opening 126 of side lumen 150 is formed by cutting the tubing 118 to be flush with surface of sheath 112. Tubing 118 is positioned in place by a mandrel inserted into lumen 112b and secured in place by a solvent. Tip 112a is formed in a similar manner as in introducer 10.

Equivalents

While this invention has been particularly shown and described with references to preferred embodiments thereof, it will be understood by those skilled in the art that various changes in form and details may be made therein without departing from the spirit and scope of the invention as defined by the appended claims.

We claim:

1. A method for introducing a catheter and a large volume of fluids into a body lumen with a multi-lumen percutaneous introducer comprising the steps of:

passing a catheter through an introducer sheath, the introducer sheath having a first lumen, the first lumen having a proximal opening a distal opening through which the catheter is passed and an inner diameter of about 8.5 French;

delivering fluids into the body lumen with a second introducer sheath lumen, the second lumen having a proximal opening for receiving fluids and a distal opening for delivering the fluids and having an internal size of at least 14 gauge; and advancing the catheter through an introducer port and the sheath, the introducer port being in alignment with the first lumen within the sheath.

2. The method of claim 1 further comprising the step of sealing the first lumen with a valve assembly in alignment with the first lumen and the introducer port.

3. The method of claim 1 further comprising the step of delivering fluid into the first lumen with a side port.

4. The method of claim 3 further comprising the step of directing fluid into the side port with a directional valve coupled in fluid communication with the side port.

5. The method of claim 1 in which the sheath is made of extruded polyurethane.

6. A method for introducing a catheter and a large volume of fluids into a body lumen with a multi-lumen percutaneous introducer comprising the steps of:

positioning a guidewire percutaneously into a body lumen;

sliding a catheter introducer and dilator over the guidewire to position a distal end of the introducer within the body lumen;

removing the dilator from the introducer; and passing a catheter through the introducer, the introducer having a first lumen, the first lumen having a proximal opening, a distal opening through which the catheter is passed and an inner diameter of about 8.5 French; and delivering fluids into the body lumen with a second introducer lumen, the second lumen having a proximal opening for receiving fluids and a distal opening for delivering the fluids and further having an internal size of at least 14 gauge.

7. The method of claim 6 further comprising the step of sealing the first lumen with a valve assembly in alignment with the first lumen and the introducer port.

8. The method of claim 6 further comprising the step of delivering fluid into the first lumen with a side port.

9. The method of claim 8 further comprising the step of directing fluid into the side port with a directional valve coupled in fluid communication with the side port.

10. The method of claim 6 further comprising providing an introducer made of extruded polyurethane.

11. The method of claim 6 delivering a drug through the second lumen.

* * * * *